United States Patent [19]

Forner et al.

[11] Patent Number: 5,565,447
[45] Date of Patent: Oct. 15, 1996

[54] INDOLE DERIVATIVES

[75] Inventors: Dolors F. Forner; Carles P. Duran; Jose P. Soto; Armando V. Noverola; Jacinto M. Mauri, all of Barcelona, Spain

[73] Assignee: Laboratorios Almirall S.A., Spain

[21] Appl. No.: 437,682

[22] Filed: May 9, 1995

Related U.S. Application Data

[63] Continuation of Ser. No. 211,446, Mar. 28, 1994, abandoned.

[30] Foreign Application Priority Data

Jul. 28, 1992 [GB] United Kingdom .................. 9216009

[51] Int. Cl.⁶ ...................... A61K 31/445; A61K 31/495; C07D 401/12; C07D 403/12
[52] U.S. Cl. .......................... 514/212; 514/253; 514/323; 514/414; 514/235.2; 540/602; 544/143; 544/373; 546/201; 548/467
[58] Field of Search ........................... 548/467; 544/373; 546/201; 540/602; 514/212, 253, 323, 414

[56] References Cited

FOREIGN PATENT DOCUMENTS

| | | |
|---|---|---|
| 0303506A2 | 2/1989 | European Pat. Off. . |
| 2082175 | 3/1982 | United Kingdom . |
| 2124210 | 2/1984 | United Kingdom . |
| 2162532 | 2/1986 | United Kingdom . |
| 2168347 | 6/1986 | United Kingdom . |
| 91/18897 | 12/1991 | WIPO . |

OTHER PUBLICATIONS

Gonzalez, A., "A Convenient Preparation of 8-Ethyl-4, 9-Dihydro-3H-Pyrano[3,4-b]Indole-1-One, Key Intermediate of the Antiinflammatory Agent Etodolac," *Synthetic Communications*, 21(5), pp. 669-674 (1991).
Howell, B. A., "A Convenient Method for the Preparation of 2,4-Dinitrophenylhydrazones," *Journal of Chemical Education*, p. 176 (1984).
Plieninger, H., "Eine Synthese des Tryptophans," from the Research Laboratory of Knoll A. G., Ludwigshafen, vol. 83, pp. 268-271 (Jan. 23, 1950).
Humphrey, P. P. A. et al., "GR43175, a selective agonist for the 5-$HT_1$-like receptor in dog isolated saphenous vein," *Br. J. Pharmacol.*, vol. 94, pp. 1123-1132, (1988).
Bruinvels, A. T., et al., "5-$HT_{1D}$ binding sites in various species: similar pharmacological profile in dog, monkey, calf, guinea-pig and human brain membranes", *Naunyn-Schmiedeberg's Arch Pharmacol*, vol. 346, pp. 243-248 (1992).

Gozlan, H. et al., "Identification of presynaptic serotonin autoreceptors using a new ligand: ³H-PAT," *Nature*, vol. 305, pp. 140-143 (Sep. 8, 1983).

Sundberg et al, *J. Org. Chem.* 53 p. 5097 (1988).

Primary Examiner—Emily Bernhardt
Attorney, Agent, or Firm—Spencer & Frank

[57] ABSTRACT

A compound of formula (I)

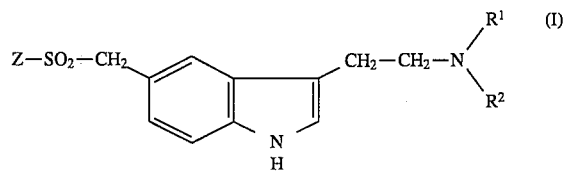

wherein $R^1$ and $R^2$ each represents a hydrogen atom or an alkyl group, Z represents a ring selected from:

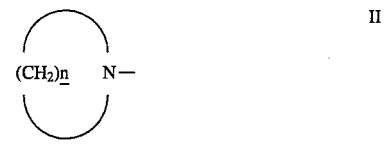

in which $\underline{n}$ represents 4, 5 or 6;

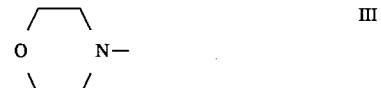

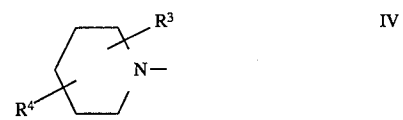

in which $R^3$ represents hydrogen or an alkyl group and $R^4$ represents an alkyl, methoxy benzyl or $R^5$ NHCO group, $R^5$ being an alkyl group; and

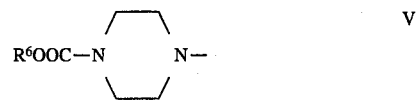

in which $R^6$ represents an alkyl group.
and pharmaceutically acceptable salts thereof are useful in the treatment of migraine and other conditions. They are prepares by decarboxylation of the corresponding indolyl 2-carboxylic acid.

6 Claims, No Drawings

INDOLE DERIVATIVES

This application is a continuation of application Ser. No. 08/211,446, filed Mar. 28, 1994, now abandoned which application is a 371 of PCT/EP93/01901 filed Jul. 19, 1993.

THIS INVENTION relates to new indol derivatives, methods for their preparation, compositions containing them and their use in medical treatment.

The mechanism involved in the genesis of a migraine attack is not known, but it has been demonstrated that the large intracranial vessels are distended during the headache phase. Some compounds like ergotamine and serotonine (5-Hydroxytryptamine; 5-HT), have a vasoconstrictor action in the carotid vascular bed by an agonistic action at the "5-$HT_1$-like" receptors. However, the lack of selectivity of these compounds is the cause of undesirable and potentially dangerous side-effects.

In British Patents 2124210A and 2162532A, new anti-migraine compounds have been disclosed and seem to stimulate more selectively a sub-population of "5-$HT_1$-like" receptors. Among these compounds, Sumatriptan of formula:

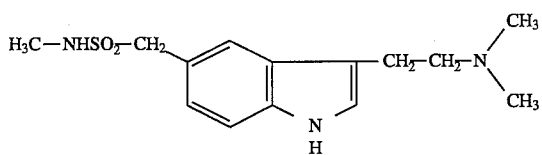

is available for migraine therapy. This compound presents a high affinity for 5-$HT_{1D}$ receptor but it has also a very important affinity for 5-$HT_{1A}$ receptor. This affinity for 5-$HT_{1A}$ receptor, causes hypotension by a central nervous system action and other side effects.

We have now found that the introduction of a nitrogen ring in the methanesulfonyl group provides new anti-migraine compounds that present a greater affinity for 5-$HT_{1D}$ receptor than for 5-$HT_{1A}$ receptor and therefore, less side-effects.

Accordingly, the present invention provides a compound of formula:

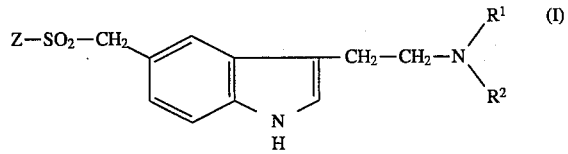

wherein $R^1$ and $R^2$ each represent a hydrogen atom or an alkyl group, Z represents a ring selected from:

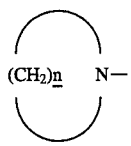

in which n represents 4, 5 or 6;

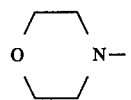

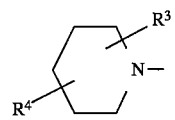

in which $R^3$ represents hydrogen or an alkyl group $R^4$ represents an alkyl, methoxy, benzyl or $R^5$ NHCO group, $R^5$ being an alkyl group; and

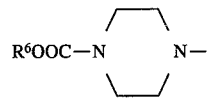

in which $R^6$ represents an alkyl group; and pharmaceutically acceptable salts thereof.

The alkyl group mentioned in relation with the groups $R^1$, $R^2$, $R^3$, $R^4$, $R^5$ and $R^6$ in compounds of the invention, are usually "lower" alkyl, that is containing up to 6 and particularly up to 4 carbon atoms, the hydrocarbon chain being branched or straight.

The compounds of general formula I wherein $R^1$ and $R^2$ are alkyl groups and Z is II or V are preferred.

According to a feature of the present invention the indol derivatives of general formula I may be prepared by the process which comprises a decarboxylation of a carboxylic acid of general formula VI:

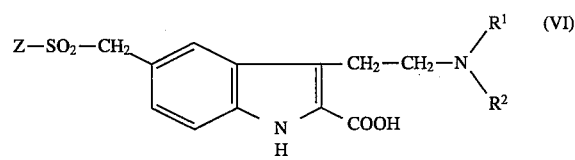

(wherein the various symbols are as defined above). The reaction is preferably carried out in an inert organic solvent as quinoline, tri-n-butylamine, N,N-dimethylacetamide or pyridine, in the presence of a catalyst as copper powder, cupric oxide, cuprous oxide or other copper derivatives, at a temperature between 100° and 200° C.

The intermediates VI used in the preparation of the compounds of the invention, were prepared by known processes described in the literature (A. Gonzalez, Synth. Commun. (1991)), 21, 669; B. A. Howell, J. Chem. Ed. 176 (1984); H. Plieninger, Ber. (1950), 83, 268).

Indol derivatives of general formula I can be converted by methods known per se into acid addition salts with acids in appropriate solvents, for example acetone, alcohols, dioxane or tetrahydrofuran. Suitable acid addition salts are those derived from inorganic acids, for example the hydrochlorides and sulphates.

The experiments with usual test animals were conducted and evaluated in the following manner:

Dog Saphenous Vein

Isometric recordings were performed essentially as described by Humphrey et al (1988). Briefly, lateral saphenous vein ring preparations (3 mm. wide) removed from anaesthetized beagle dogs were suspended under 2g. resting tension, in 30 mL organ baths containing Krebs at 37° C. The experiments were carried out in the presence of 5-HT2, H1 and muscarinic antagonists and serotonin 1 µM was used as quantitative reference standard.

(Humphrey P. P. A.; Feniuk W.; Perren M. J.; Connor H. E.; Oxford A. W .; Coates I. H. and Butina D. (1988). GR 43175, a selective agonist for the 5-HT1-like receptor in dog isolated saphenous vein. Br. J. Pharmac. 94, 1123–1132).

Binding to 5HT1D Receptors

Assays were performed essentially as described by Bruinvels et al. Varying amounts of tested drugs were added to 0.25 mL final volume reaction that included 100 µg of calf caudate nucleus membrane protein, 100 pM (Serotonin-5-0-Carboxymethyl-Glycyl[$^{125}$I]Tyrosinamide ($^{125}$I-GTI), 4 mM $CaCl_2$ and 50 mM Tris HCl buffer, pH 7.4. After incubation at 37° C. for 30 minutes, samples were filtered under reduced pressure using glass fibre filters. The filters were washed with ice-cold buffer and dried. Non-specific binding was defined as that obtained in the presence of 10 µM 5HT. Trapped radioactivity was quantified using a gamma counter. Displacement curves were constructed and the concentration displacing 50% of radioligand was calculated for each tested compound using non-linear regression. Data from at least three different assays run in duplicate was averaged. (Bruinvels A. T.; Lery H.; Palacios J. M. and Hoyer D. 5-$HT_{1D}$ binding sites in various species: similar pharmacological profile in dog, monkey, calf, guinea-pig and human brain membranes. Naunyn-Schmiedeberg's Arch. Pharmacol. (in press)).

Binding to 5HT1A receptors

Assays were performed essentially as described by Gozlan et al (1983). Varying amounts of tested drugs were added to 1 mL final volume reaction mixtures that included 100 µg of rat hippocampus membrane protein, 0.5 nM $^3$H-8-OH-DPAT, 4 mM $CaCl_2$, 0.1% ascorbic acid, 10 µM pargyline and 50 mM Tris HCl buffer, pH 7.4. After incubation at 25° C. for 30 minutes, samples were filtered under reduced pressure using glass fibre filters. The filters were washed with ice-cold buffer and dried. Non-specific binding was defined as that obtained in the presence of 10 µM 5HT. Radioactivity was quantified by scintillation counting and data was handled as described for the 5$HT_{1D}$ binding assay. (Gozlan H.; El Mestikawy S.; Pichat L.; Glowinski J. and Hamon M. (1983). Identification of presynaptic serotonin autoreceptors using a new ligand:$^3$H-PAT. Nature 305, 140–142).

The results of the tests described above, using compounds according to the invention (see Examples below) and, as a comparison, Sumatriptan, are shown in Table I below:

TABLE I

Results of different pharmacological test

| | Dog saphenous vein pD2 | Binding IC50 nM | | |
|---|---|---|---|---|
| | | 125I-GTI | 3H-8-OH-DPAT | 5HT1A/ 5HT1D |
| Sumatriptan | 6.06 ± 0.01 | 10.4 ± 1 | 460 ± 67 | 44.2 |
| 1 | 6.06 ± 0.03 | 10.7 ± 0.4 | 825 ± 69 | 77.1 |
| 2 | 5.92 ± 0.10 | 6.9 ± 0.4 | 340 ± 0.5 | 49.3 |
| 11 | 6.47 ± 0.03 | 3.2 ± 0.3 | 850 ± 40 | 265.6 |

From results presented above it can be concluded that the novel compounds of this invention demonstrate binding selectivity for 5-HT1D receptors and vasoconstrictor capability mediated by an agonism on 5HT1D receptors. According to the results this invention provides compounds with potential interest for the treatment or prevention of migraine and other headache associated with vascular disorders (e.g. cluster headache and chronic paroxysmal hemicrania), with administration of substances or their withdrawal, and for the treatment or prevention of tensional cephaliar pain, movement disorders, depression and anxiety.

Thus, the present invention provides indol derivatives of the formula I and pharmaceutically acceptable salts thereof, and pharmaceutical compositions comprising such derivatives and salts thereof, for use in the treatment or therapy of the human body.

Accordingly, the indol derivatives of the formula I and pharmaceutically acceptable salts thereof, and pharmaceutical compositions comprising such derivatives and salts thereof, may be used in a method of treatment of disorders of the human body which comprises administering to a recipient in need of such therapy an effective amount of said derivatives or salts thereof or said compositions.

The present invention also provides pharmaceutical compositions which comprise, as active ingredient, at least one compound of general formula I, or a pharmacologically acceptable salt in association with a pharmaceutically acceptable carrier or diluent. The active ingredient may comprise 0.001% to 99% by weight, preferably 0.01% to 90% by weight of the composition depending upon the nature of the formulation and whether further dilution is to be made prior to application. Preferably the compositions are made up in a form suitable for oral, topical, percutaneous or parenteral administration.

The pharmaceutically acceptable carriers or diluents which are admixed with the active compound, or compounds or salts of such compounds, to form the compositions of this invention are well-known per se and the actual excipients used depend inter alia on the intended method of administering the compositions. Compositions of this invention are preferably adapted for administration parenteral and per os. In this case, the composition for oral administration may take the form of tablets, capsules or liquid preparations, such as mixtures, elixirs, syrups or suspensions, all containing one or more compounds of the invention; such preparations may be made by methods well-known in the art.

The diluents which may be used in the preparation of the compositions include those liquid and solid diluents which are compatible with the active ingredient, together with colouring or flavouring agents, if desired. Tablets or capsules may conveniently contain between 1 and 200 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in water or an appropriate parenteral injection fluid.

Effective doses are normally in the range of 10–600 mg of active ingredient per day.

The following Examples illustrate the preparation of compounds of the present invention.

EXAMPLE 1

To a solution of previously dried 1-[[2-carboxy-3-(2-dimethylaminoethyl)-5-indolyl]methanesulphonyl]pyrrolidine (1.6 g; 0.0442 moles) in anhydrous quinoline (75 ml) and under atmosphere of nitrogen, cuprous oxide (160 mg; 0.0011 moles) was added. The reaction mixture was heated to 190° C. for 15 minutes, stirred to room temperature, poured into a mixture of 1N hydrochloric acid (150 ml) and ethyl acetate (50 ml), shaken and decanted. The aqueous solution was washed several times with ethyl acetate, then solid sodium bicarbonate was added until pH=7.8, and washed with n-hexane to eliminate the quinoline. The aqueous solution was made alkaline with solid potassium carbonate and extracted with ethyl acetate. The organic solution was dried ($Na_2SO_4$), the solvent removed under reduced pressure when a dark oil was obtained (1.3 g; yield 92%). This product was purified by column chromatography with silica gel and methylene chloride:ethanol:ammonium hydroxide (60:8:1) as eluent and a white foam (0.8 g) of 1-[[3-(2-dimethylaminoethyl)-5-indolyl]methanesulphonyl]pyrrolidine was obtained.

To a solution of the above product (0.8 g) in acetone (30 ml), a few drops of hydrogen chloride saturated dioxan solution, were added. The precipitated solid was collected by filtration, washed with acetone and dried to give 1-[[3-(2-dimethylaminoethyl)-5-indolyl]methanesulphonyl]-pyrrolidine hydrochloride (0.75 g). Melting point 218°–220° C.

Further indol derivatives of general formula I as set out in Table 2 below were prepared according to the process disclosed in Example 1 but using the appropriately substituted reactants VI.

TABLE 2

| COMPOUND No. | $R^1$; $R^2$ | Z | DERIVATIVE | M.P °C. |
|---|---|---|---|---|
| 1 | $R^1 = R^2 = CH_3$ | II; n = 4 | HCl | 218–220 |
| 2 | $R^1 = R^2 = CH_3$ | II; n = 5 | HCl | 225–227(d) |
| 3 | $R^1 = R^2 = CH_3$ | II; n = 6 | hydrogen succinate | 127–130(d) |
| 4 | $R^1 = H$; $R^2 = CH_3$ | II; n = 4 | HCl | 177–178 |
| 5 | $R^1 = R^2 = CH_3$ | III | HCl | 231–232(d) |
| 6 | $R^1 = R^2 = CH_3$ | IV; $R^3 = H$; $R^4 = 4\text{-}CH_3$ | hydrogen succinate | 151–153 |
| 7 | $R^1 = R^2 = CH_3$ | IV; $R^3 = R^4 = 4\text{-}CH_3$ | hydrogen succinate | 170–172 |
| 8 | $R^1 = R^2 = CH_3$ | IV; $R^3 = H$; $R^4 = $ methoxy | hydrogen succinate | 143–145 |
| 9 | $R^1 = R^2 = CH_3$ | IV; $R^3 = H$; $R^4 = $ benzyl | HCl | 225–227 |
| 10 | $R^1 = R^2 = CH_3$ | IV; $R^3 = H$; $R^4 = H_3CNHCO$ | base | 161–163 |
| 11 | $R^1 = R^2 = CH_3$ | V; $R^6 = C_2H_5$ | base | 170–171 |

EXAMPLE 2

20,000 Ampoules each containing 10 mg. of 1-[[3-(2-dimethylaminoethyl)-5-indolyl]methanesulphonyl]piperidine hydrochloride (active ingredient) were prepared from the following formulation:

| Active ingredient | 200 g |
|---|---|
| Sodium chloride | 200 g |
| Water injectable grade q.s. | 40 liters |

Procedure

The active ingredient and sodium chloride were dissolved in 40 litres of water, then passed through a bacteria-retaining filter and filled under sterile conditions into 2 ml glass ampoules in known manner.

We claim:

1. A compound of formula (I)

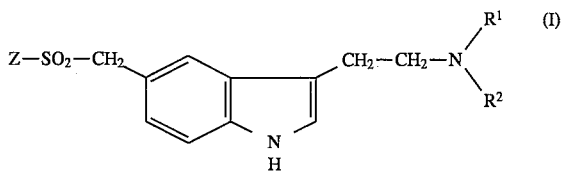

wherein $R^1$ and $R^2$ each represents a hydrogen atom or a $C_{1-6}$ alkyl group, Z represents a ring selected from:

in which $\underline{n}$ represents 4, 5 or 6;

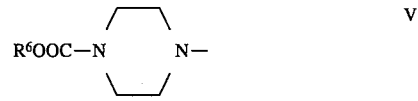

in which R6 represents a $C_{1-6}$ alkyl group,
or pharmaceutically acceptable salts thereof.

2. A compound according to claim 1 in which $R^1$ and $R^2$ which by the same or different is each $C_{1-4}$ alkyl, and Z is of the formula II.

3. 1-[[3-(2-dimethylaminoethyl)-5-indolyl]methanesulphonyl]pyrrolidine;

1-[[3-(2-dimethylaminoethyl)-5-indolyl]methanesulphonyl]piperidine; or

1-[[3-(2-dimethylaminoethyl)-5-indolyl]methanesulphonyl]-4-ethoxycarbonyl piperazine; or a hydrochloride salt thereof.

4. A composition comprising a compound according to claim 1 mixed with a pharmaceutically acceptable carrier or diluent.

5. A method of treating headaches, movement disorders, depression or anxiety which comprises administering to a human or animal subject in need of treatment of an effective amount of a compound according to claim 1.

6. A method according to claim 5 wherein said treatment is for a migraine.

* * * * *

UNITED STATES PATENT AND TRADEMARK OFFICE
CERTIFICATE OF CORRECTION

PATENT NO. : 5,565,447
DATED : October 15, 1996
INVENTOR(S) : Dolors F. Forner; Carles P. Duran; Jose P. Soto; Armando V. Noverola; Jacinto M. Mauri It is certified that error appears in the above-indentified patent and that said Letters Patent is hereby corrected as shown below:

Title page:
Item 63: DELETE "Continuation of Ser. No. 211,446, Mar. 28, 1994, abandoned" INSERT, therefor:

--Continuation of Ser. No. 211,446, filed Mar. 28, 1994, abandoned, which is a 371 of PCT/EP93/01901, filed July 19, 1993.--

Signed and Sealed this

Eleventh Day of March, 1997

Attest:

BRUCE LEHMAN

*Attesting Officer*     Commissioner of Patents and Trademarks

UNITED STATES PATENT AND TRADEMARK OFFICE
CERTIFICATE OF CORRECTION

PATENT NO.  : 5,565,447
DATED       : Oct. 15, 1996
INVENTOR(S) : Dolors F. Forner, et al It is certified that error appears in the above-indentified patent and that said Letters Patent is hereby corrected as shown below:

Column 1:

Line 62, DELETE "nrepresents"  INSERT, therefor:

--n represents--

Column 6:  Line 34, DELETE "which by the same"  INSERT, therefor:

--which are the same--.

Signed and Sealed this

Ninth Day of September, 1997

Attest:

BRUCE LEHMAN

Attesting Officer

Commissioner of Patents and Trademarks